US012753134B2

(12) United States Patent
Cambrodon et al.

(10) Patent No.: US 12,753,134 B2
(45) Date of Patent: Oct. 6, 2026

(54) PROCESS FOR THE PRODUCTION OF TRIFLUOROETHYLENE

(71) Applicant: ARKEMA FRANCE, Colombes (FR)

(72) Inventors: Alexandre Cambrodon, Pierre-Benite (FR); Thierry Lannuzel, Pierre-Benite (FR); Cédric Lavy, Pierre-Benite (FR); Philippe Leduc, Pierre-Benite (FR); Kevin Hisler, Pierre-Benite (FR)

(73) Assignee: ARKEMA FRANCE, Puteaux (FR)

( * ) Notice: Subject to any disclaimer, the term of this patent is extended or adjusted under 35 U.S.C. 154(b) by 561 days.

(21) Appl. No.: 18/250,620

(22) PCT Filed: Oct. 27, 2021

(86) PCT No.: PCT/FR2021/051883
§ 371 (c)(1),
(2) Date: Apr. 26, 2023

(87) PCT Pub. No.: WO2022/096804
PCT Pub. Date: May 12, 2022

(65) Prior Publication Data

US 2023/0391693 A1 Dec. 7, 2023

(30) Foreign Application Priority Data

Nov. 3, 2020 (FR) ....................................... 2011263

(51) Int. Cl.
*C07C 17/23* (2006.01)
*B01J 23/44* (2006.01)

(52) U.S. Cl.
CPC ............... *C07C 17/23* (2013.01); *B01J 23/44* (2013.01)

(58) Field of Classification Search
CPC ........ C07C 17/23; C07C 17/354; C07C 21/18
See application file for complete search history.

(56) References Cited

U.S. PATENT DOCUMENTS

2016/0002518 A1 1/2016 Taniguchi et al.
2018/0251414 A1* 9/2018 Terazono ................. B01J 23/60

FOREIGN PATENT DOCUMENTS

EP 0053657 A1 6/1982
EP 2993213 A1 3/2016
WO 2013128102 A1 9/2013
WO 2014178352 A1 11/2014

OTHER PUBLICATIONS

International Search Report (PCT/ISA/210) with English translation and Written Opinion (PCT/ISA/237) mailed on Feb. 25, 2022, by the European Patent Office as the International Searching Authority for International Application No. PCT/FR2021/051883.
Office Action (Notice of Reasons for Refusal) issued on Aug. 4, 2025, by the Japanese Patent Office in corresponding Japanese Patent Application No. 2023-526542, and an English Translation of the Office Action. (14 pages).

* cited by examiner

*Primary Examiner* — Medhanit W Bahta
(74) *Attorney, Agent, or Firm* — Buchanan Ingersoll & Rooney PC

(57) ABSTRACT

The present invention relates to a process for the production of trifluoroethylene in a reactor equipped with a fixed catalytic bed comprising a catalyst, said process comprising a stage a) of reaction of chlorotrifluoroethylene with hydrogen in the presence of the catalyst and in the gas phase in order to produce a stream comprising trifluoroethylene; said stage a) being carried out at a temperature of the fixed catalytic bed T1 of between 50° C. and 250° C.; said process being characterized in that, during stage a), the temperature of the fixed catalytic bed T1 is increased provided that it does not exceed 300° C.

16 Claims, No Drawings

PROCESS FOR THE PRODUCTION OF TRIFLUOROETHYLENE

TECHNICAL FIELD

The present invention relates to a process for the production of hydrofluoroolefins. In particular, the present invention relates to a process for the production of trifluoroethylene by hydrogenolysis of chlorotrifluoroethylene ($VF_3$).

TECHNOLOGICAL BACKGROUND OF THE INVENTION

Fluorinated olefins, such as $VF_3$, are known and are used as monomers or comonomers for the manufacture of fluorocarbon polymers exhibiting noteworthy characteristics, in particular excellent chemical resistance and good heat resistance.

Trifluoroethylene is a gas under standard conditions of pressure and temperature. The main risks associated with the use of this product relate to its flammability, its propensity for self-polymerization when it is not stabilized, its explosiveness due to its chemical instability and its supposed sensitivity to peroxidation, by analogy with other halogenated olefins. Trifluoroethylene exhibits the distinguishing feature of being extremely flammable, with a lower explosive limit (LEL) of approximately 10% and an upper explosive limit (UEL) of approximately 30%. The major danger, however, is associated with the propensity of $VF_3$ to decompose violently and explosively under certain pressure conditions in the presence of an energy source, even in the absence of oxygen.

Given the main risks above, the synthesis and also the storage of $VF_3$ pose particular problems and impose strict safety rules throughout these processes. A known route for the preparation of trifluoroethylene uses, as starting materials, chlorotrifluoroethylene (CTFE) and hydrogen in the presence of a catalyst and in the gas phase. There is known, from WO2013/128102, a process for the production of trifluoroethylene by hydrogenolysis of CTFE in the gas phase and in the presence of a catalyst based on a metal from group VIII at atmospheric pressure and at relatively low temperatures. However, there is a need for a more effective process for the production of trifluoroethylene.

SUMMARY OF THE INVENTION

The present invention relates to a process for the production of trifluoroethylene in a reactor equipped with a fixed catalytic bed comprising a catalyst, said process comprising a stage a) of reaction of chlorotrifluoroethylene with hydrogen in the presence of the catalyst and in the gas phase in order to produce a stream comprising trifluoroethylene; said stage a) being carried out at a temperature of the fixed catalytic bed T1 of between 50° C. and 250° C.;

said process being characterized in that, during stage a), the temperature of the fixed catalytic bed T1 is increased provided that it does not exceed 300° C.

The present invention makes it possible to provide an efficient process for the production of trifluoroethylene. In particular, the present invention makes possible an increase in the conversion over time. The implementation of the present process is particularly important when the activity of the catalyst decreases excessively. The increase in the temperature of the fixed catalytic bed drastically increases the activity of the catalyst, which would otherwise have continued to decrease. The present invention thus makes it possible to maintain a high productivity of trifluoroethylene over time and makes it possible to avoid excessively frequent phases of regeneration of the catalyst, which would impact the overall productivity of the process. Thus, the present invention provides a process for controlling the temperature of the reaction so as to prolong the lifetime of the catalyst and to thus improve the overall efficiency of the process.

According to a preferred embodiment, the temperature of the fixed catalytic bed T1 does not exceed 290° C., advantageously does not exceed 280° C., preferably does not exceed 270° C., more preferentially does not exceed 260° C., in particular does not exceed 250° C.

According to a preferred embodiment, the temperature of the fixed catalytic bed T1 is increased by a value of between 0° C. and 50° C., advantageously between 5° C. and 50° C., preferably between 5° C. and 45° C., more preferentially between 10° C. and 45° C., in particular between 10° C. and 40° C.

According to a preferred embodiment, during stage a), the temperature of the fixed catalytic bed T1 is increased by a value of between 0° C. and 50° C., preferably between 5° C. and 45° C., up to a temperature T1a; said temperature T1a being maintained for a period of time of greater than 30 min, preferably of greater than 1 h.

According to a preferred embodiment, during the reaction of stage a), at a moment t, the longitudinal temperature difference between the inlet of the fixed catalytic bed and the outlet of the fixed catalytic bed is less than 20° C.

According to a preferred embodiment, said catalyst is a catalyst based on a metal from columns 8 to 10 of the Periodic Table of the Elements, deposited on a support based on aluminum or on carbon; in particular, said catalyst is palladium supported on $\alpha$-alumina.

According to a preferred embodiment, the hydrogen is introduced into the reactor at a temperature of between 30° C. and 240° C.

According to a preferred embodiment, the chlorotrifluoroethylene is introduced into the reactor at a temperature of between 30° C. and 240° C.

According to a preferred embodiment, stage a) is carried out at a pressure of less than 2 bar.

According to a preferred embodiment, the flow rate for introduction of the hydrogen or the flow rate for introduction of the CTFE or both into the reactor is reduced in order to increase the temperature of the fixed catalytic bed T1.

According to a preferred embodiment, the reactor is equipped with a jacket comprising a heat-transfer fluid in order to control the temperature of the fixed catalytic bed T1 and said temperature of the jacket T2 is of between 0° C. and 200° C.

According to a preferred embodiment, the temperature of the jacket T2 is of between 0° C. and 180° C., advantageously between 5° C. and 160° C., preferably between 10° C. and 140° C., in particular between 15° C. and 120° C., more particularly between 20° C. and 100° C.

According to a preferred embodiment, during stage a), the temperature of the jacket of the reactor T2 is increased by a value of between 0° C. and 50° C., advantageously between 5° C. and 50° C., preferably between 5° C. and 45° C., more preferentially between 10° C. and 45° C., in particular between 10° C. and 40° C.

According to a preferred embodiment, during stage a), the temperature of the jacket of the reactor T2 is increased by a value of between 0° C. and 50° C. up to a temperature T2a; said temperature T2a being maintained for a period of time of greater than 30 min, preferably of greater than 1 h.

According to a preferred embodiment, said reactor comprises a plurality of tubes each comprising at least one fixed catalytic bed containing said catalyst.

According to a preferred embodiment, said reactor comprises a jacket and a plurality of tubes each comprising at least one fixed catalytic bed containing said catalyst.

According to a preferred embodiment, said reactor comprises a plurality of tubes each comprising at least one fixed catalytic bed containing said catalyst; each of said tubes being equipped with a jacket comprising a heat-transfer fluid.

DETAILED DESCRIPTION OF THE PRESENT INVENTION

The present invention relates to a process for the production of trifluoroethylene. Said process is carried out in a reactor equipped with a fixed catalytic bed comprising a catalyst.

The present invention comprises, as mentioned above, a stage of reaction of chlorotrifluoroethylene (CTFE) with hydrogen (stage a) or hydrogenolysis stage). The hydrogenolysis stage is carried out in the presence of a catalyst and in the gas phase. Thus, said process comprises a stage a) of reaction of chlorotrifluoroethylene with hydrogen in the presence of the catalyst and in the gas phase in order to produce a stream comprising trifluoroethylene.

The hydrogenolysis stage consists in simultaneously introducing hydrogen, CTFE and optionally an inert gas, such as nitrogen, in the gas phase and in the presence of said catalyst.

Preferably, said stage a) is carried out at a temperature of the fixed catalytic bed T1 of between 50° C. and 250° C. Said stage a) can be carried out at a temperature of the fixed catalytic bed T1 of between 50° C. and 240° C., advantageously between 50° C. and 230° C., preferably between 50° C. and 220° C., more preferentially between 50° C. and 210° C., in particular between 50° C. and 200° C. Said stage a) can also be carried out at a temperature of the fixed catalytic bed T1 of between 60° C. and 250° C., advantageously between 70° C. and 250° C., preferably between 80° C. and 250° C., more preferentially between 90° C. and 250° C., in particular between 100° C. and 250° C., more particularly between 120° C. and 250° C. Said stage a) can also be carried out at a temperature of the fixed catalytic bed T1 of between 60° C. and 240° C., advantageously between 70° C. and 230° C., preferably between 80° C. and 220° C., more preferentially between 90° C. and 210° C., in particular between 100° C. and 200° C., more particularly between 100° C. and 180° C., favorably between 100° C. and 160° C., particularly preferably between 120° C. and 160° C.

During the implementation of stage a), the catalyst used for the reaction between the CTFE and the hydrogen loses activity. In order to regain a better catalytic activity, and thus a better productivity, during stage a), the temperature of the fixed catalytic bed T1 is increased by a value of between 0° C. and 50° C.

Preferably, in the present process, during stage a), the temperature of the fixed catalytic bed T1 is increased provided that it does not exceed 300° C.

The temperature of the fixed catalytic bed T1 is preferably controlled so as not to exceed 250° C.

This makes it possible to avoid side reactions and to avoid the formation of undesired coproducts. Preferably, the temperature of the fixed catalytic bed T1 does not exceed 249° C., does not exceed 248° C., does not exceed 247° C., does not exceed 246° C., does not exceed 245° C., does not exceed 244° C., does not exceed 243° C., does not exceed 242° C., does not exceed 241° C., does not exceed 240° C., does not exceed 239° C., does not exceed 238° C., does not exceed 237° C., does not exceed 236° C., does not exceed 235° C., does not exceed 234° C., does not exceed 233° C., does not exceed 232° C., does not exceed 231° C., does not exceed 230° C., does not exceed 229° C., does not exceed 228° C., does not exceed 227° C., does not exceed 226° C., does not exceed 225° C., does not exceed 224° C., does not exceed 223° C., does not exceed 222° C., does not exceed 221° C., does not exceed 220° C., does not exceed 219° C., does not exceed 218° C., does not exceed 217° C., does not exceed 216° C., does not exceed 215° C., does not exceed 214° C., does not exceed 213° C., does not exceed 212° C., does not exceed 211° C., does not exceed 210° C., does not exceed 209° C., does not exceed 208° C., does not exceed 207° C., does not exceed 206° C., does not exceed 205° C., does not exceed 204° C., does not exceed 203° C., does not exceed 202° C., does not exceed 201° C., does not exceed 200° C.

In particular, the temperature of the fixed catalytic bed T1 is controlled so as not to exceed 200° C. This makes it possible to avoid side reactions and to avoid the formation of undesired coproducts. Preferably, the temperature of the fixed catalytic bed T1 does not exceed 199° C., does not exceed 198° C., does not exceed 197° C., does not exceed 196° C., does not exceed 195° C., does not exceed 194° C., does not exceed 193° C., does not exceed 192° C., does not exceed 191° C., does not exceed 190° C., does not exceed 189° C., does not exceed 188° C., does not exceed 187° C., does not exceed 186° C., does not exceed 185° C., does not exceed 184° C., does not exceed 183° C., does not exceed 182° C., does not exceed 181° C., does not exceed 180° C., does not exceed 179° C., does not exceed 178° C., does not exceed 177° C., does not exceed 176° C., does not exceed 175° C., does not exceed 174° C., does not exceed 173° C., does not exceed 172° C., does not exceed 171° C., does not exceed 170° C., does not exceed 169° C., does not exceed 168° C., does not exceed 167° C., does not exceed 166° C., does not exceed 165° C., does not exceed 164° C., does not exceed 163° C., does not exceed 162° C., does not exceed 161° C., does not exceed 160° C., does not exceed 159° C., does not exceed 158° C., does not exceed 157° C., does not exceed 156° C., does not exceed 155° C., does not exceed 154° C., does not exceed 153° C., does not exceed 152° C., does not exceed 151° C., does not exceed 150° C.

According to a preferred embodiment, the temperature of the fixed catalytic bed T1 is increased by a value of 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. The increase in the temperature of the fixed catalytic bed makes it possible to increase the conversion of the reaction between CTFE and hydrogen.

The temperature of the fixed catalytic bed T1 can be increased by a value of between 0° C. and 50° C., advantageously between 2° C. and 50° C., preferably between 4° C. and 50° C., more preferentially between 6° C. and 50° C., in particular between 8° C. and 50° C., more particularly between 10° C. and 50° C. The temperature of the fixed catalytic bed T1 can be increased by a value of between 0° C. and 49° C., advantageously between 2° C. and 49° C., preferably between 4° C. and 49° C., more preferentially between 6° C. and 49° C., in particular between 8° C. and 49° C., more particularly between 10° C. and 49° C. The temperature of the fixed catalytic bed T1 can be increased by a value of between 0° C. and 48° C., advantageously between 2° C. and 48° C., preferably between 4° C. and 48° C., more preferentially between 6° C. and 48° C., in particular between 8° C. and 48° C., more particularly between 10° C. and 48° C. The temperature of the fixed catalytic bed T1 can be increased by a value of between 0° C. and 47° C., advantageously between 2° C. and 47° C., preferably between 4° C. and 47° C., more preferentially between 6° C. and 47° C., in particular between 8° C. and 47° C., more particularly between 10° C. and 47° C. The temperature of the fixed catalytic bed T1 can be increased by a value of between 0° C. and 46° C., advantageously between 2° C. and 46° C., preferably between 4° C. and 46° C., more preferentially between 6° C. and 46° C., in particular between 8° C. and 46° C., more particularly between 10° C. and 46° C. The temperature of the fixed catalytic bed T1 can be increased by a value of between 0° C. and 45° C., advantageously between 2° C. and 45° C., preferably between 4° C. and 45° C., more preferentially between 6° C. and 45° C., in particular between 8° C. and 45° C., more particularly between 10° C. and 45° C. The temperature of the fixed catalytic bed T1 can be increased by a value of between 0° C. and 44° C., advantageously between 2° C. and 44° C., preferably between 4° C. and 44° C., more preferentially between 6° C. and 44° C., in particular between 8° C. and 44° C., more particularly between 10° C. and 44° C. The temperature of the fixed catalytic bed T1 can be increased by a value of between 0° C. and 43° C., advantageously between 2° C. and 43° C., preferably between 4° C. and 43° C., more preferentially between 6° C. and 43° C., in particular between 8° C. and 43° C., more particularly between 10° C. and 43° C. The temperature of the fixed catalytic bed T1 can be increased by a value of between 0° C. and 42° C., advantageously between 2° C. and 42° C., preferably between 4° C. and 42° C., more preferentially between 6° C. and 42° C., in particular between 8° C. and 42° C., more particularly between 10° C. and 42° C. The temperature of the fixed catalytic bed T1 can be increased by a value of between 0° C. and 41° C., advantageously between 2° C. and 41° C., preferably between 4° C. and 41° C., more preferentially between 6° C. and 41° C., in particular between 8° C. and 41° C., more particularly between 10° C. and 41° C. The temperature of the fixed catalytic bed T1 can be increased by a value of between 0° C. and 40° C., advantageously between 2° C. and 40° C., preferably between 4° C. and 40° C., more preferentially between 6° C. and 40° C., in particular between 8° C. and 40° C., more particularly between 10° C. and 40° C.

Thus, the temperature of the fixed catalytic bed T1 is increased up to a temperature T1a. The increase in the temperature of the fixed catalytic bed T1 to the temperature T1a can thus be carried out stepwise. Said temperature T1a is maintained for a period of time of greater than 30 min, advantageously of greater than 1 h, preferably of greater than 5 h, more preferentially of greater than 10 h, in particular of greater than 20 h, more particularly of greater than 50 h. The reaction between CTFE and hydrogen thus exhibits a better conversion after having increased the temperature of the fixed catalytic bed from the temperature T1 to T1a.

The temperature of the fixed catalytic bed T1 can be controlled by different means. For example, if the reactor comprises a jacket, the temperature of the fixed catalytic bed can be controlled by the temperature of the jacket. The temperature of the fixed catalytic bed can also be controlled by the management of the pressure between the inlet and the outlet of the reactor, or by the management of the flow rates for introduction of the reactants within the reactor or by the temperature for introduction of the reactants into the reactor or by the dilution of the reactants with an inert flow.

According to a preferred embodiment, the pressure at the inlet of the fixed catalytic bed is greater than the pressure at the outlet of the fixed catalytic bed. Stage a) is preferably carried out at a pressure of less than 4 bar, preferably of less than 2 bar, in particular at a pressure of between 400 mbar and 1 bar. In addition to controlling the temperature of the fixed catalytic bed T1, this also makes it possible to control the risks associated with the explosiveness of the trifluoroethylene produced during the hydrogenolysis reaction.

According to another preferred embodiment, the temperature of the fixed catalytic bed T1 can be controlled by the temperature at which the hydrogen and the CTFE are introduced into the reactor. During stage a), the temperature of introduction of the hydrogen and the temperature of introduction of the CTFE into the reactor can be increased in order to increase the temperature of the fixed catalytic bed T1 by a value as mentioned above. According to a preferred embodiment, the temperature of introduction of the hydrogen into the reactor is of between 20° C. and 250° C. The temperature of introduction of the hydrogen into the reactor is of between 30° C. and 240° C., advantageously between 40° C. and 230° C., preferably between 50° C. and 220° C., more preferentially between 50° C. and 210° C., in particular between 50° C. and 200° C. The temperature of introduction of the hydrogen into the reactor is of between 60° C. and 200° C., advantageously between 70° C. and 200° C., preferably between 80° C. and 200° C., more preferentially between 90° C. and 200° C., in particular between 100° C. and 200° C., more particularly between 120° C. and 200° C., favorably between 130° C. and 200° C., advantageously favorably between 140° C. and 200° C., preferentially favorably between 150° C. and 200° C. According to a preferred embodiment, the temperature of introduction of the CTFE into the reactor is of between 20° C. and 250° C. The temperature of introduction of the CTFE into the reactor is of between 30° C. and 240° C., advantageously between 40° C. and 230° C., preferably between 50° C. and 220° C., more preferentially between 50° C. and 210° C., in particular between 50° C. and 200° C. The temperature of introduction of the CTFE into the reactor is of between 60° C. and 200° C., advantageously between 70° C. and 200° C., preferably between 80° C. and 200° C., more preferentially between 90° C. and 200° C., in particular between 100° C. and 200° C., more particularly between 120° C. and 200° C., favorably between 130° C. and 200° C., advantageously favorably between 140° C. and 200° C., preferentially favorably between 150° C. and 200° C. The temperature of introduction of the hydrogen into the reactor or the temperature of introduction of the CTFE into the reactor, or both, can be increased so as to increase the temperature of the fixed catalytic bed T1 by a value of between 0° C. and 50° C. The temperature of introduction of hydrogen into the reactor and the temperature of introduction of the CTFE into the reactor are thus adapted accordingly in order to achieve the desired increase in the temperature of the fixed catalytic bed.

According to another preferred embodiment, the temperature of the fixed catalytic bed T1 can be controlled by the flow rate at which the hydrogen and the CTFE are introduced into the reactor. For example, the flow rate for introduction of the hydrogen or the flow rate for introduction of the CTFE or both can be reduced in order to increase the temperature of the fixed catalytic bed T1.

According to another preferred embodiment, the temperature of the fixed catalytic bed can be controlled by the dilution of the reactants with an inert flow. The inert flow can be a nitrogen flow, a flow comprising HCl optionally resulting from the recycling of the HCl produced during stage a), or a recycling flow comprising organic compounds produced during stage a).

According to another preferred embodiment, said reactor is also equipped with a jacket comprising a heat-transfer fluid. The circulation of the heat-transfer fluid in the jacket of the reactor makes it possible to control the temperature within the catalytic bed. Thus, in this embodiment, the temperature of the jacket of the reactor T2 is of between 0° C. and 200° C. Preferably, the temperature of the jacket of the reactor T2 is of between 0° C. and 180° C., advantageously between 0° C. and 160° C., preferably between 0° C. and 140° C., in particular between 0° C. and 120° C., more particularly between 0° C. and 100° C. The temperature of the jacket of the reactor T2 can also be of between 5° C. and 180° C., preferably between 10° C. and 180° C., in particular between 15° C. and 180° C., more particularly between 20° C. and 180° C. The temperature of the jacket of the reactor T2 can also be of between 5° C. and 160° C., preferably between 10° C. and 140° C., in particular between 15° C. and 120° C., more particularly between 20° C. and 100° C.

According to a preferred embodiment, the temperature of the jacket of the reactor T2 is increased by a value of 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. The temperature of the jacket of the reactor T2 can be increased by a value of between 0° C. and 50° C., advantageously between 2° C. and 50° C., preferably between 4° C. and 50° C., more preferentially between 6° C. and 50° C., in particular between 8° C. and 50° C., more particularly between 10° C. and 50° C. The temperature of the jacket of the reactor T2 can be increased by a value of between 0° C. and 49° C., advantageously between 2° C. and 49° C., preferably between 4° C. and 49° C., more preferentially between 6° C. and 49° C., in particular between 8° C. and 49° C., more particularly between 10° C. and 49° C. The temperature of the jacket of the reactor T2 can be increased by a value of between 0° C. and 48° C., advantageously between 2° C. and 48° C., preferably between 4° C. and 48° C., more preferentially between 6° C. and 48° C., in particular between 8° C. and 48° C., more particularly between 10° C. and 48° C. The temperature of the jacket of the reactor T2 can be increased by a value of between 0° C. and 47° C., advantageously between 2° C. and 47° C., preferably between 4° C. and 47° C., more preferentially between 6° C. and 47° C., in particular between 8° C. and 47° C., more particularly between 10° C. and 47° C. The temperature of the jacket of the reactor T2 can be increased by a value of between 0° C. and 46° C., advantageously between 2° C. and 46° C., preferably between 4° C. and 46° C., more preferentially between 6° C. and 46° C., in particular between 8° C. and 46° C., more particularly between 10° C. and 46° C. The temperature of the jacket of the reactor T2 can be increased by a value of between 0° C. and 45° C., advantageously between 2° C. and 45° C., preferably between 4° C. and 45° C., more preferentially between 6° C. and 45° C., in particular between 8° C. and 45° C., more particularly between 10° C. and 45° C. The temperature of the jacket of the reactor T2 can be increased by a value of between 0° C. and 44° C., advantageously between 2° C. and 44° C., preferably between 4° C. and 44° C., more preferentially between 6° C. and 44° C., in particular between 8° C. and 44° C., more particularly between 10° C. and 44° C. The temperature of the jacket of the reactor T2 can be increased by a value of between 0° C. and 43° C., advantageously between 2° C. and 43° C., preferably between 4° C. and 43° C., more preferentially between 6° C. and 43° C., in particular between 8° C. and 43° C., more particularly between 10° C. and 43° C. The temperature of the jacket of the reactor T2 can be increased by a value of between 0° C. and 42° C., advantageously between 2° C. and 42° C., preferably between 4° C. and 42° C., more preferentially between 6° C. and 42° C., in particular between 8° C. and 42° C., more particularly between 10° C. and 42° C. The temperature of the jacket of the reactor T2 can be increased by a value of between 0° C. and 41° C., advantageously between 2° C. and 41° C., preferably between 4° C. and 41° C., more preferentially between 6° C. and 41° C., in particular between 8° C. and 41° C., more particularly between 10° C. and 41° C. The temperature of the jacket of the reactor T2 can be increased by a value of between 0° C. and 40° C., advantageously between 2° C. and 40° C., preferably between 4° C. and 40° C., more preferentially between 6° C. and 40° C., in particular between 8° C. and 40° C., more particularly between 10° C. and 40° C. Thus, the temperature of the jacket of the reactor T2 is increased up to a temperature T2a. Said temperature T2a is maintained for a period of time of greater than 30 min, advantageously of greater than 1 h, preferably of greater than 5 h, more preferentially of greater than 10 h, in particular of greater than 20 h, more particularly of greater than 50 h.

According to a preferred embodiment, during stage a), the longitudinal temperature difference between the inlet of the fixed catalytic bed and the outlet of the fixed catalytic bed can be less than 20° C., at a given moment t. The value of the longitudinal temperature difference is considered as an absolute value. The longitudinal temperature difference is defined by the temperature difference between the inlet of the fixed catalytic bed and the outlet of the fixed catalytic bed. Preferably, the longitudinal temperature difference between the inlet of the fixed catalytic bed and the outlet of the fixed catalytic bed can be less than 19° C., preferably less than 18° C., more preferentially less than 17° C., in particular less than 16° C., more particularly less than 15° C., favorably less than 14° C., advantageously favorably less than 13° C., preferentially favorably less than 12° C., more preferentially favorably less than 11° C., particularly favorably less than 10° C. Thus, by controlling in particular the longitudinal temperature between the inlet and the outlet of the fixed catalytic bed, a good productivity is obtained and the formation of undesirable coproducts is limited.

In addition, during the reaction of stage a), the temperature difference between a point located at the center of the fixed catalytic bed and a point located in the radial plane can optionally be less than 150° C., at a given moment t. The value of the radial temperature difference is considered as an absolute value. The radial temperature difference between a point located at the center of the fixed catalytic bed and a point located in the radial plane can optionally be less than 140° C., preferably less than 130° C., more preferentially less than 120° C., in particular less than 110° C., more particularly less than 100° C., favorably less than 90° C., advantageously favorably less than 80° C., preferentially favorably less than 70° C., more preferentially favorably less than 60° C., particularly favorably less than 50° C. The radial temperature difference can optionally be less than 40° C., advantageously less than 30° C., preferably less than 20° C.

Preferably, the catalyst is based on a metal from columns 8 to 10 of the Periodic Table of the Elements. In particular, the catalyst is based on a metal selected from the group consisting of Pd, Pt, Rh, and Ru; preferably palladium. Preferably, the catalyst is supported. The support is preferably selected from the group consisting of activated carbon, alumina, calcium carbonate and graphite. Preferably, the support is based on aluminum. In particular, the support is alumina. Thus, the catalyst is more particularly palladium supported on alumina.

The alumina can be α-alumina. Preferably, the alumina comprises at least 90% of α-alumina. It was observed that the conversion of the hydrogenolysis reaction was improved when the alumina is an α-alumina.

Preferably, the palladium represents from 0.01% to 5% by weight based on the total weight of the catalyst, preferably from 0.1% to 2% by weight, based on the total weight of the catalyst. Said catalyst is preferably activated before its use in stage a). Preferably, the activation of the catalyst is carried out at high temperature and in the presence of a reducing agent. According to a specific embodiment, the reducing agent is chosen from the group consisting of hydrogen, carbon monoxide, nitrogen monoxide, formaldehyde, $C_1$-$C_6$ alkanes and $C_1$-$C_{10}$ hydrohalocarbons, or a mixture of these; preferably hydrogen or a $C_1$-$C_{10}$ hydrohalocarbon, or a mixture of these; in particular hydrogen, chlorotrifluoroethylene, trifluoroethylene, chlorotrifluoroethane, trifluoroethane or difluoroethane, or a mixture of these. Preferably, the activation of the catalyst is carried out at a temperature of between 100° C. and 400° C., in particular at a temperature of between 150° C. and 350° C.

According to a preferred embodiment, in stage a), the $H_2$/CTFE newly introduced or initially introduced molar ratio is of between 0.5/1 and 2/1 and preferably of between 1/1 and 1.2/1. If an inert gas, such as nitrogen, is present in stage a), the nitrogen/$H_2$ molar ratio is of between 0/1 and 2/1 and preferably of between 0/1 and 1/1.

The contact time, calculated as being the ratio of the volume, in liters, of catalyst to the total flow rate of the gas mixture, in standard liters per second, at the inlet of the reactor, is of between 1 and 60 seconds, preferably between 5 and 45 seconds, in particular between 10 and 30 seconds, more particularly between 15 and 25 seconds. The contact time can also make it possible to control the temperature of the fixed catalytic bed T1. The increase in the temperature of the fixed catalytic bed during stage a) can be regulated by increasing the contact time.

Preferably, the process is carried out continuously. The increase in the temperature of the fixed catalytic bed during stage a) is preferably implemented without halting the reaction of stage a). Preferably, in stage a), the hydrogen is in anhydrous form. Preferably, in stage a), the chlorotrifluoroethylene is in anhydrous form. The implementation of the present process in the presence of anhydrous hydrogen and/or chlorotrifluoroethylene makes it possible to effectively increase the lifetime of the catalyst and thus the overall productivity of the process. The term anhydrous refers to a content by weight of water of less than 1000 ppm, advantageously 500 ppm, preferably of less than 200 ppm, in particular of less than 100 ppm, based on the total weight of the compound under consideration.

Stage a) of hydrogenolysis of CTFE results in the production of a stream A comprising trifluoroethylene. Said stream A can also comprise unreacted hydrogen and unreacted CTFE. The stream A can also comprise trifluoroethane and/or chlorotrifluoroethane as byproducts of the hydrogenolysis reaction. The stream A can also comprise HCl and HF. Preferably, the stream A is recovered at the reactor outlet in the gaseous form.

The present process can also comprise a stage b) of purification of said stream A. Said purification comprises stages targeted at removing the byproducts of the reaction. Thus, at the outlet of the hydrogenolysis reactor, the stream A is treated in order to remove HCl and HF. The stream A is passed through water in a scrubbing column followed by scrubbing with a dilute base, such as NaOH or KOH. The remainder of the gas mixture, consisting of the unconverted reactants ($H_2$ and CTFE), dilution nitrogen (if present) and reaction products ($VF_3$, F143, F133 and other organic products) which form the gas mixture B, is directed to a dryer in order to remove the traces of scrubbing water. Drying can be carried out using products such as calcium, sodium or magnesium sulfate, calcium chloride, potassium carbonate, silica gel or zeolites. In one embodiment, a molecular sieve (zeolite), such as siliporite, is used for the drying. The stream B, thus dried, is subjected to a stage of separation of the hydrogen and inert substances from the remainder of the other products present in the mixture B, by absorption/desorption in the presence of an alcohol comprising from 1 to 4 carbon atoms and preferably ethanol, at atmospheric pressure and at a temperature below ambient temperature, preferably of less than 10° C. and more preferably still at a temperature of −25° C., for the absorption. In one embodiment, the absorption of the organic substances is carried out in a countercurrent column with ethanol cooled to −25° C. The ethanol flow rate is adjusted according to the flow rate of organic substances to be absorbed. The hydrogen and inert gases, which are insoluble in ethanol at this temperature, are removed at the absorption column top. The organic substances are subsequently recovered in the form of a gas mixture C, by heating the ethanol to its boiling point (desorption), in order to be subsequently distilled.

Pure trifluoroethylene ($VF_3$) is subsequently distilled from the mixture C, to be separated from the other organic products (CTFE, F143, F133 and other organic substances, forming a mixture D). The mixture D comprising the other organic compounds is recovered at the column bottom. The distillation of said mixture D on a second column makes it possible to recover and recycle the unconverted CTFE at the column top and to remove the byproducts of the reaction at the bottom of this second column.

EXAMPLES

100 $cm^3$ of catalyst (0.2% of palladium supported on α-alumina) are introduced into a tubular reactor consisting of a stainless steel tube with a length of 1200 mm over a diameter of 25 mm, and equipped with a jacket. The catalyst, thus charged, is subsequently activated in the following way: the reaction tube is placed in a tube furnace and is fed with a stream of nitrogen (from 0.5 to 2 mol/h). The fixed catalytic bed is then heated to a temperature of 250° C. After this activation period, the tube is cooled to ambient temperature and then is isolated in order to then be installed on a hydrogenolysis test bench. The reactor is fed with 116 g/h of CTFE and 2 g/h of hydrogen. It is also possible to feed the reactors with an inert gas (in this instance nitrogen). The contact time, calculated as being the ratio of the volume in liters of catalyst to the sum of the flow rates of the reactants in standard liters per second, is of the order of 22 seconds. Table 1 shows the $VF_3$ productivity as a function of the temperature.

TABLE 1

| Test | Temperature of the jacket | Duration of the reaction (h) | $VF_3$ productivity (g/h) |
|---|---|---|---|
| 1 | 25° C. | 30 | 100 |
| 2 | 25° C. | 30 | 75 |
| 3 | 35° C. | 40 | 88 |
| 4 | 50° C. | 72 | 94 |

As illustrated in Table 1, in particular by comparing test 1 and test 2, the $VF_3$ productivity decreases over time due to a deactivation of the catalyst. The temperature of the jacket was then increased by 10° C. (test 3). After 40 hours of reaction, the $VF_3$ productivity was 88 g/h, i.e. a productivity gain of close to 20% with respect to test 2, during which the temperature was 25° C. By again increasing the temperature of the jacket from 35° C. to 50° C., the $VF_3$ productivity increased from 88 g/h to 94 g/h (test 3 vs test 4). The process according to the present invention makes it possible to provide a process which is efficient over time with a good conversion of the CTFE and a good $VF_3$ selectivity.

The invention claimed is:

1. A process for the production of trifluoroethylene in a reactor equipped with a fixed catalytic bed comprising a catalyst, said process comprising a stage a) of reaction of chlorotrifluoroethylene (CTFE) with hydrogen in the presence of the catalyst and in the gas phase in order to produce a stream comprising trifluoroethylene; said stage a) being carried out at a temperature of the fixed catalytic bed T1 of between 50° C. and 250° C.;

wherein, during stage a), the temperature of the fixed catalytic bed T1 is increased provided that it does not exceed 300° C., and wherein the flow rate for introduction of the hydrogen or the flow rate for introduction of the CTFE or both into the reactor is reduced in order to increase the temperature of the fixed catalytic bed T1.

2. The process as claimed in claim 1, wherein the temperature of the fixed catalytic bed T1 is increased by a value of between 5° C. and 45° C.

3. The process as claimed in claim 1, wherein the temperature of the fixed catalytic bed T1 does not exceed 290° C.

4. The process as claimed in claim 1, wherein the temperature of the fixed catalytic bed T1 is increased by a value of between 5° C. and 40° C.

5. The process as claimed in claim 1, wherein, during stage a), the temperature of the fixed catalytic bed T1 is increased by a value of between 5° C. and 45° C. up to a temperature T1a; said temperature T1a being maintained for a period of time of greater than 30 min.

6. The process as claimed in claim 1, wherein, during the reaction of stage a), at a given moment t, the longitudinal temperature difference between the inlet of the fixed catalytic bed and the outlet of the fixed catalytic bed is less than 20° C.

7. The process as claimed in claim 1, wherein said catalyst is a catalyst based on a metal from columns 8 to 10 of the Periodic Table of the Elements, deposited on a support based on aluminum or on carbon.

8. The process as claimed in claim 7, wherein said catalyst is palladium supported on α-alumina.

9. The process as claimed in claim 1, wherein the hydrogen is introduced into the reactor at a temperature of between 30° C. and 240° C.

10. The process as claimed in claim 1, wherein the chlorotrifluoroethylene is introduced into the reactor at a temperature of between 30° C. and 240° C.

11. The process as claimed in claim 1, wherein stage a) is carried out at a pressure of less than 2 bar.

12. A process for the production of trifluoroethylene in a reactor equipped with a fixed catalytic bed comprising a catalyst, said process comprising a stage a) of reaction of chlorotrifluoroethylene with hydrogen in the presence of the catalyst and in the gas phase in order to produce a stream comprising trifluoroethylene; said stage a) being carried out at a temperature of the fixed catalytic bed T1 of between 50° C. and 250° C.;

wherein, during stage a), the temperature of the fixed catalytic bed T1 is increased provided that it does not exceed 300° C., and wherein the reactor is equipped with a jacket comprising a heat-transfer fluid in order to control the temperature of the fixed catalytic bed T1 and in that said temperature of the jacket of the reactor T2 is of between 0° C. and 200° C.

13. The process as claimed in claim 12, wherein the temperature of the jacket T2 is of between 0° C. and 180° C.

14. The process as claimed in claim 12, wherein, during stage a), the temperature of the jacket of the reactor T2 is increased by a value of between 0° C. and 50° C.

15. The process as claimed in claim 12, wherein, during stage a), the temperature of the jacket of the reactor T2 is increased by a value of between 0° C. and 50° C. up to a temperature T2*a*; said temperature T2*a* being maintained for a period of time of greater than 30 min.

16. The process as claimed in claim 12, wherein said reactor comprises a plurality of tubes each comprising at least one fixed catalytic bed containing said catalyst.

* * * * *